(12) United States Patent
Gordon (10) Patent No.: US 6,510,346 B2
(45) Date of Patent: Jan. 21, 2003

(54) THERAPEUTIC INFRARED ENERGY WRIST COVER

(75) Inventor: Lawrence Gordon, Watauga, TX (US)

(73) Assignee: Lawrence D. Gordan (*) Notice: Subject to any disclaimer, the term of this patent is extended or adjusted under 35 U.S.C. 154(b) by 55 days.

(21) Appl. No.: 09/736,544

(22) Filed: Dec. 13, 2000

(65) Prior Publication Data
US 2002/0072786 A1 Jun. 13, 2002

(51) Int. Cl.⁷ ............................ A61F 2/00; A61B 18/18
(52) U.S. Cl. .......................... 607/100; 606/10; 607/88
(58) Field of Search ......................... 607/100, 88, 90, 607/96, 108, 111; 606/2, 10, 13, 14; 602/21

(56) References Cited

U.S. PATENT DOCUMENTS

| | | |
|---|---|---|
| RE22,763 E | 6/1946 | Clark |
| 3,961,157 A | 6/1976 | Miller et al. |
| 4,162,393 A | 7/1979 | Balboni |
| 4,250,398 A | 2/1981 | Ellis et al. |
| 4,663,516 A | 5/1987 | Blum |
| 4,680,822 A | 7/1987 | Fujino et al. |
| 4,825,868 A | 5/1989 | Susa et al. |
| 5,138,138 A | 8/1992 | Theilacker et al. |
| 5,241,415 A | 8/1993 | Argentieri et al. |
| 5,259,380 A * | 11/1993 | Mendes et al. ............. 607/115 |
| 5,324,911 A | 6/1994 | Cranston et al. |
| 5,430,900 A | 7/1995 | Kim |
| 5,608,383 A | 3/1997 | Neil |
| 5,616,140 A * | 4/1997 | Prescott ........................ 606/10 |
| 5,750,962 A | 5/1998 | Hyatt |
| 6,067,404 A | 5/2000 | Wilkins et al. |
| 6,261,261 B1 | 7/2001 | Gordon |
| 6,297,481 B1 | 10/2001 | Gordon |

FOREIGN PATENT DOCUMENTS

| | | |
|---|---|---|
| CA | 1261908 | 9/1989 |
| DE | 28 26 353 A1 | 12/1979 |
| JP | 09276419 A * | 10/1997 |

OTHER PUBLICATIONS

Thermotex Equine Therapy Systems, Thermotex Personal Therapy Systems, http://www.thermotex.com, 19 pages.
Thermotex Equine Therapy Systems, Thermotex Personal Therapy Systems, http://www.thermotex.com/equine/index.htm, 12 pages.

* cited by examiner

*Primary Examiner*—Chen-Wen Jiang

(57) ABSTRACT

A therapeutic infrared emitting wrist cover 12 that provides a wrist cover 12, constructed for placement over a human wrist 10, that contains an infrared energy generating system 14. The wrist cover 12 emits infrared energy into the wrist 10 at a localized area corresponding to the carpal tunnel for the purpose of providing therapeutic heat inside the wrist 10 in order to relieve the symptoms and to prevent further trauma associated with carpal tunnel syndrome.

11 Claims, 6 Drawing Sheets

THERAPEUTIC INFRARED ENERGY WRIST COVER

TECHNICAL FIELD OF THE INVENTION

This invention relates in general to a heat generating system for the relief of pain and the reduction of trauma associated with carpal tunnel syndrome and, in particular, to an infrared energy emitting wrist cover for the purpose of providing penetrating heat localized in the subsurface carpel tunnel structure.

BACKGROUND OF THE INVENTION

Without limiting the scope of the present invention, its background is described in connection with an infrared energy generating system contained within a wrist cover. It should be noted that the principles of the present invention are applicable in a variety of embodiments, including, but not limited to, an infrared energy generating wrist pad and an infrared energy generating wrist saddle.

Heretofore, in this field, a variety of resistance heating systems have been developed to provide therapeutic heat to different areas of the body. The current state of the art in therapeutic resistance heating systems allows for application of heat conductively transferred to the surface of a traumatized area of the body through surface contact. These systems typically apply the heat generated over a broad surface area, without localizing the heat generated to the often small area traumatized. Additionally, the typical resistance heating system, usually resistance metal wire elements, causes the materials used to house the heating system to become hot, preventing much of the heat generated from serving its intended purpose of heating the traumatized body area and providing the potential for the housing to cause burns to the surface of the skin.

The current state of the art in therapeutic resistance heating systems often employs a large, "bulky" heating pad unit. The heat generated in these heating pads is often wasted through heat transfer with the air and heat transfer to areas of the body not affected by the particular injury. The electrical resistance heat is typically dissipated and diffused through insulative material covering the electrical resistance wire and is applied to the surface of the affected area. The injury, however, is typically below the surface in joints, tendons, muscles, and in the osteofibrous material bounding the carpal tunnel, the flexor tendons, and the median nerve.

Because of this inefficient use of the heat generated, the power required to supply ample heat to the traumatized area is often greater than what should be necessary if the heat were localized to a small area. This inefficiency causes the power supply to become a limiting factor in how long and where these heating pads may be used. For example, if batteries are used to supply power to the heating pads, the inefficiency of such pads provides a shortened battery life for the corresponding amount of heat applied to the traumatized area. Similarly, if a standard 120 volt electrical wall outlet is used to overcome the problems associated with batteries as a power supply, the electric power cord becomes a limiting factor on where the heating pad may be used. Freedom of movement is restricted and persons using such pads are constrained to use them within close proximity to a standard electrical outlet.

With the exponential rise in computer usage over the past decade, the number of injuries associated with keyboard usage has shown a dramatic rise as well. The most well-documented of these injuries is carpal tunnel syndrome.

Each year, thousands of employees suffer the painful and often debilitating effects of carpal tunnel syndrome. It is estimated that over the past several years, corporations in the United States have spent hundreds-of-millions of dollars in the treatment and prevention of carpal tunnel syndrome for employees.

Carpal tunnel syndrome is a nerve related condition caused by pressure on the median nerve at the point at which it passes through the carpal tunnel of the wrist. The pressure on the median nerve is caused by the angular placement of the hands relative to the wrists while typing combined with the repetitive motion of the wrist and fingers required while typing, which often causes the carpal tunnel to constrict and reduce the area in which the tendons of the wrist can operate. The pressure on the median nerve caused by prolonged constriction of the carpal tunnel produces soreness, tenderness, and weakness of the muscles of the thumb.

In the past, anti-inflammatory drugs, including corticosteroids, cortisone, and non-steroidal drugs, have been injected under the carpal tunnel, but not in the median nerve itself, to relieve the discomfort associated with carpal tunnel syndrome. Relief of the constriction of the carpal tunnel and the corresponding pressure on the median nerve can avoid reagrivation of the condition and can help the condition to heal, relieving the paresthesia, tingling, numbness, and pain associated with the condition. Often, surgery is required to correct the condition when drug therapy has not been successful, cannot be used, or cannot be safely continued for a sufficient period of time to allow healing.

Therefore, a need has arisen for a therapeutic system that is capable of reducing inflammation for an extended period of time in the carpal tunnel of the wrist. A need has also arisen for such a therapeutic system that can be used continuously without limiting a person's ability to type or perform everyday functions. Further, a need has arisen for a therapeutic heat generating system that generates and applies the heat efficiently such that the power supply is not a limiting factor in potential applications of the system. The present invention addresses these issues and provides significant advantages over the prior art, which will become more apparent to one skilled in the art through the description and drawings that follow.

SUMMARY OF THE INVENTION

The present invention achieves certain advantages over the prior art in that it specifically addresses trauma to the carpal tunnel area inside the wrists. The compact size, portability, and potential for continuous application of the instant invention make it ideal for use by all persons at risk for carpal tunnel syndrome. Specifically, when a person uses a keyboard for long periods of time, the risk of trauma to the carpal tunnel can be reduced or an existing condition can be treated by fastening the infrared energy emitting wrist cover around the wrist.

When the wrist cover fastener is fastened around the wrist, the power source is enabled, and the power transmission wires supply low voltage electrical power to the infrared energy generating system. The energy generated by the infrared energy generating matrix localizes radiant heat in the carpal tunnel area inside the wrist. Because of the unique structure of the infrared energy generating system, the radiant infrared energy penetrates into the tissue and provides localized heat inside the wrist without excessively increasing the surface temperature of the wrist cover. The heat inside the wrist causes the carpal tunnel to expand and, thus, reduces the effects of the constriction of the carpal tunnel typically associated with the angular placement of the hands relative to the wrists and the repetitive motion associated with typing. By varying the composition of the materials used in the infrared energy generating matrix, the amount of heat generated can be increased without requiring additional power. Additionally, alternative embodiments allow for the automatic shut-off of the infrared energy generating system when a maximum temperature is reached and for the indication of whether the power supply is enabled.

BRIEF DESCRIPTION OF THE DRAWINGS

For a more complete understanding of the present invention, including its features and advantages, reference is now made to the detailed description of the invention, taken in conjunction with the accompanying drawings of which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and are not intended to limit the scope of the invention.

Figure 1:
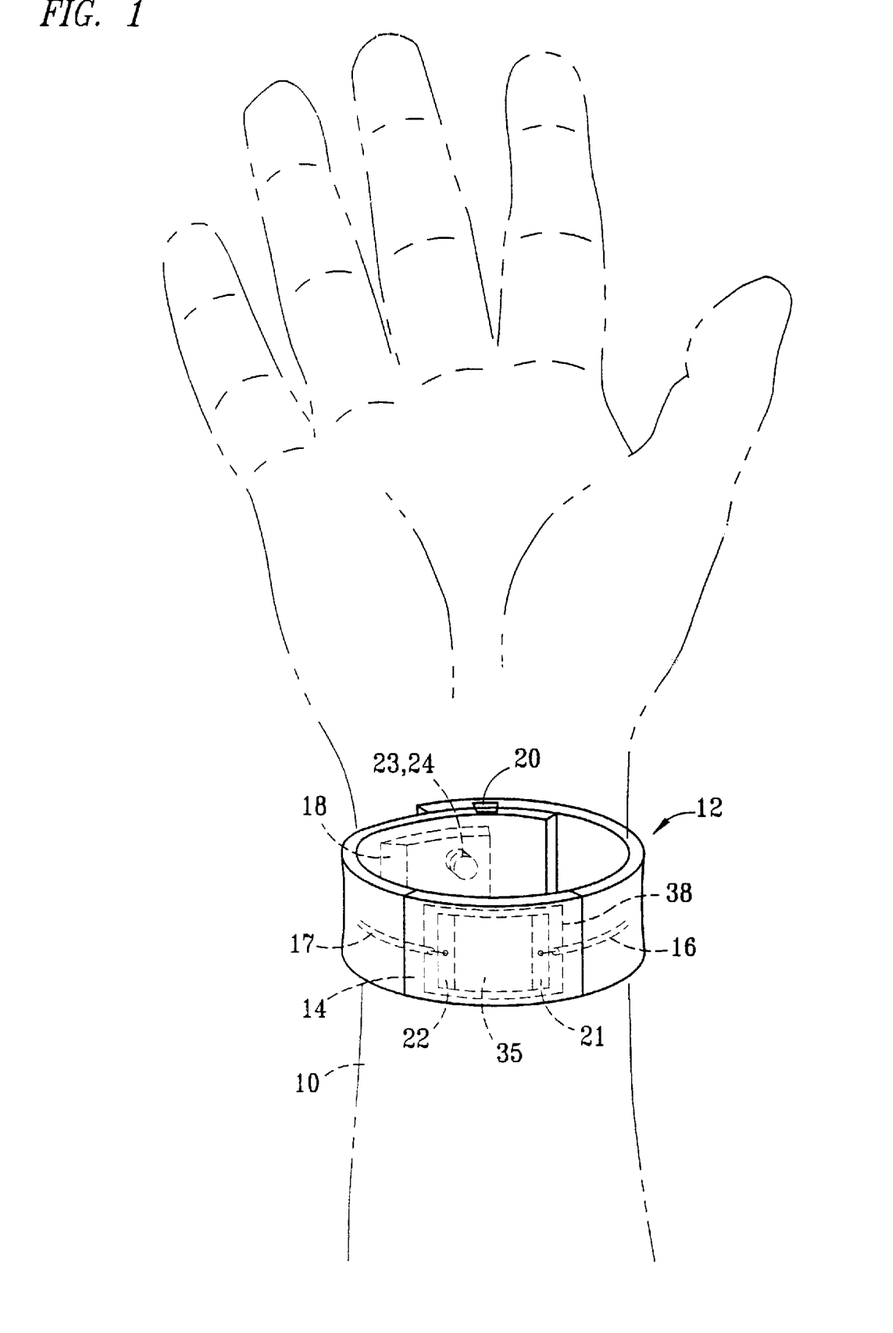
FIG. 1 is a schematic illustration of an infrared emitting wrist cover fastened around a wrist according to the present invention.

Referring to FIG. 1, a therapeutic infrared emitting wrist cover is schematically illustrated and generally designated 12. FIG. 1 shows an infrared emitting wrist cover 12 fastened around a wrist 10 shown in phantom lines. In this embodiment, a wrist cover fastener 20 provides for connection of wrist cover 12 around the wrist 10 so that a power source 18 is coupled, at contacts 23 and 24, to supply power to an infrared energy generating system 14 via power transmission wires 16 and 17. The power transmission wires are connected to the infrared energy generating system 14 at power strips 22 and 23 to activate the infrared energy generation matrix 35 interposed between the electrically powered power strips 22 and 23. When so connected around the wrist, the infrared energy generating system 14 provides infrared energy that is emitted directly into the wrist for the purpose of providing localized heat to the carpel tunnel area inside the wrist to relieve pain and to reduce further trauma associated with carpel tunnel syndrome. The unique construction of the infrared energy generating system 14, having an infrared energy generating matrix 35 and a matrix enclosure 38 connected to the power transmission wires 16 and 17 will be discussed more fully below with reference to FIG. 4.

Figure 2:
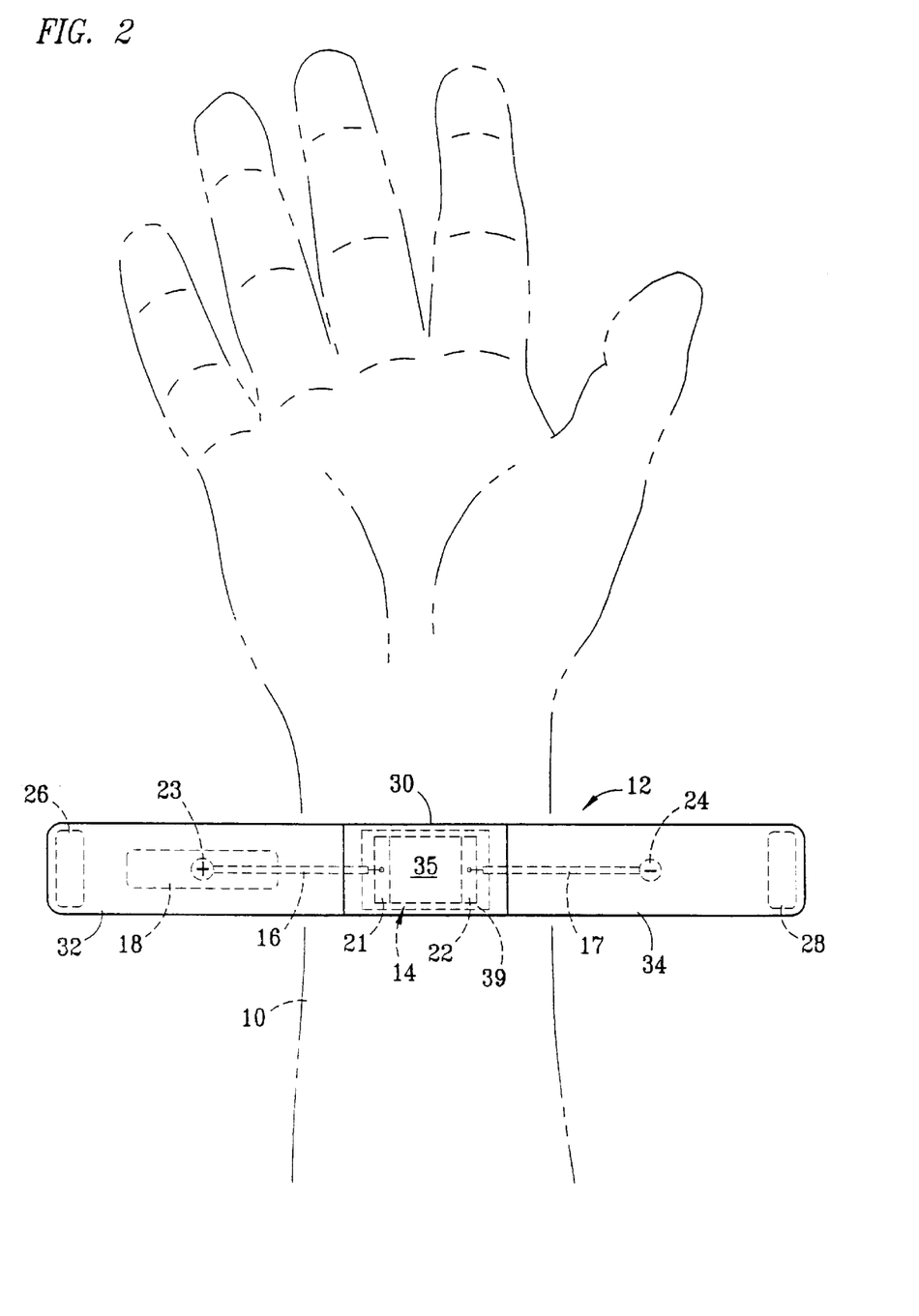
FIG. 2 is a top view schematic illustration of an infrared emitting wrist cover showing the individual elements of the present invention.

FIG. 2 is a top view schematic illustration of the infrared emitting wrist cover 12. FIG. 2 shows the individual elements of the wrist cover 12. When the wrist cover 12 is placed around the wrist 10, a first fastening device 26 and a second fastening device 28 are wrapped around the wrist 10 and fastened together. When so configured, the first electrical contact 23 comes into contact with the second electrical contact 24 such that the power source 18 is enabled and power is transmitted through the power transmission wires 16 and 17 to the infrared energy generating system 14. References to the power source 18 and the contacts 23 and 24 assume such power source to be an extended-life battery. In order to prolong the life of the power source, the battery can be made in the shape of a portion of an arc such that the battery follows the curvature of the wrist. Advantageously, by making the battery in this shape, the battery can be larger without being an encumbrance. Thus, the operational life of the infrared emitting wrist cover 12 is prolonged before the power source 18 must be changed. Additionally, the mobility of the wrist cover 12 is facilitated by the low profile of the curved power source 18.

FIG. 2 further depicts the first fastening device 26 and the second fastening device 28 attached to the ends of a first wrist cover band 32 and a second wrist cover band 34, respectively. The fastening devices 26 and 28 may be opposed pieces of the hook an loop fastening material and may extend transfers to the bands 32 and 34 or along the length of bands 32 and 34. The bands themselves may be covered with hook or the loop material so that connection at any adjusted position is possible. An infrared energy generating system housing 30 is located between the first wrist cover band 32 and the second wrist cover band 34. The infrared energy generating system 14 is located within the infrared energy generating system housing 30. As noted above, the unique construction of the infrared energy generating system 14 is discussed more fully below with reference to FIG. 4. It is interesting to note, however, that the enclosure of the infrared energy generating system 14 is a high temperature plastic material, such as a high temperature Mylar, designed for transmitting infrared energy therethrough. This material is, therefore, not subject to undue heating by the infrared energy which is transmitted directly through the Mylar enclosure without significant heat absorption so that the energy penetrates the wrist 10. This unique construction allows the inside of the wrist 10 to become heated without excessively heating the surface of the infrared energy generating system housing 30. An exterior reflective element 39, such as a polished metallic coating or foil, can facilitate reflecting the energy toward the wrist 10. Thus, the heat generated within the wrist cover 12 will not cause burns to a person's skin upon contact with the wrist 10 and efficient localized heating inside the wrist is promoted.

Figure 3:
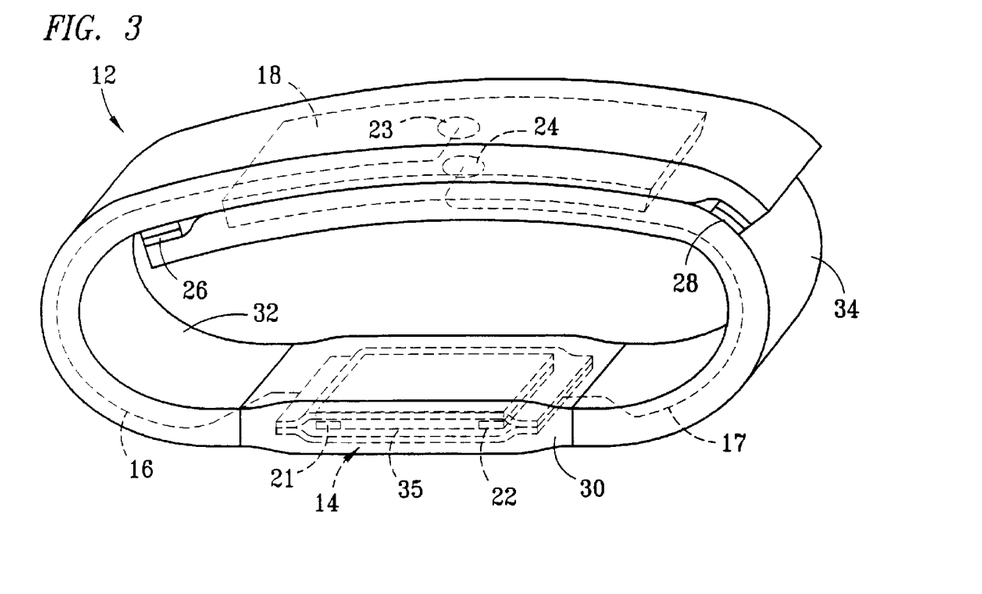
FIG. 3 is a side view schematic illustration of an infrared emitting wrist cover showing the individual elements of the present invention.
Figure 4:
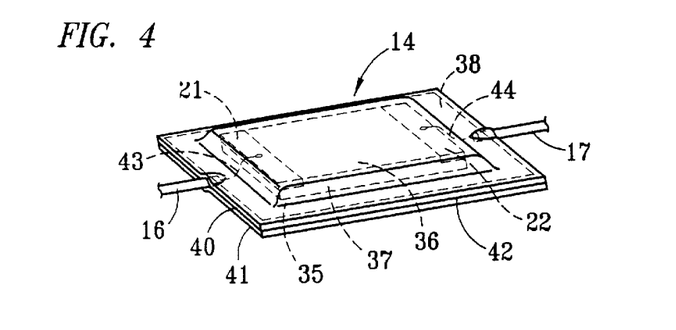
FIG. 4 is a detailed schematic illustration of an infrared energy generating system according to the present invention.

FIG. 3 is a side view schematic illustration of the wrist cover 12 showing the individual elements of the present invention. FIG. 3 shows a side view perspective of the location of the first fastening device 26 and the second fastening device 28, located at the ends of the first wrist cover band 32 and the second wrist cover band 34, respectively. FIG. 3 is representative of the relative thickness of the wrist cover 12 and shows the placement of the power source 18 within the wrist cover 12. FIG. 3 further shows the location and the relative thickness of the infrared energy generating system housing 30 with the infrared energy generating system 14 contained therein. Finally, FIG. 3 shows the connection of the power source 18 via the power transmission wires 16 and 17, to the infrared energy generating system 14. With reference to FIG. 4, the unique construction of the infrared energy generating system 14 according to the present invention may be more fully understood.

The infrared energy generating system 14 depicted in FIG. 4 shows the infrared energy generating matrix 35 comprising a carbon and polymer mixture, preferably graphite and Teflon, that is capable of generating infrared energy upon the application of an electrical current through the mixture. The graphite-Teflon matrix can be obtained under the tradename Thermotex. The electrical current to the infrared energy generating matrix 35 is supplied by the power transmission wires 16 and 17 connected to power strips 21 and 22, respectively. The infrared generating composition of graphite and Teflon is formed under heat and pressure into a sheet 36 that is embedded onto a support grid 37 forming the infrared energy generating matrix 35. The power transmission wires 16 and 17 connect to power strips 21 and 22 that run along opposite sides of the graphite-Teflon matrix forming a complete circuit when connected at contacts 21 and 22 to the power source 18.

FIG. 4 further shows the entire infrared energy generating matrix 35 encased or laminated within a high temperature plastic material, or matrix enclosure 38. The material of the matrix enclosure 38 may be comprised of an upper layer 40 and a lower layer 41 of high temperature Mylar that may be laminated together under heat and pressure such that high temperature lamination glue 42 interposed between layers 40 and 41 bonds the layers together to encase the infrared energy generating matrix 35, the power strips 21 and 22, and the connection ends 43 and 44 of the power transmission wires 16 and 17 into place to form the infrared energy generating system 14. The Mylar exterior of the matrix enclosure 38 is designed to transmit infrared energy without absorbing an excessive amount of the energy; thus, maintaining a normal temperature on the exterior. One type of high temperature Mylar useful in this invention is available in the form of long sheets on rolls, with a corresponding lamination glue 42 on one side so that two opposed sheets can be rolled off of adjacent rolls and pressed and bonded together at approximately 350° Fahrenheit. This material can be obtained from General Binding Corporation of Chicago, Ill.

Figure 5:
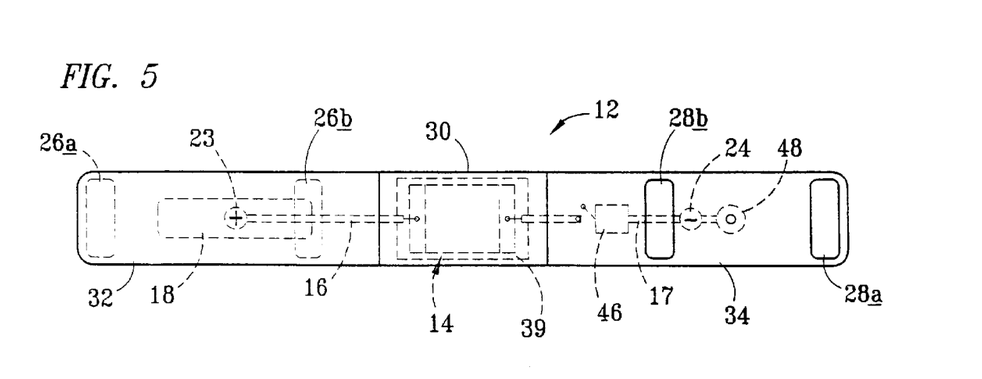
FIG. 5 is a top view schematic illustration of an alternative embodiment of an infrared emitting wrist cover showing the inclusion of a temperature controlling switch and a power source enabled indicator.

FIG. 5 shows an alternative embodiment of the wrist cover 12 with the individual features as described previously. FIG. 5, however, contains further advantages and beneficial features of the invention, namely a temperature controlling switch 46 and a power source enabled indicator 48. The temperature controlling switch 46 can be used to measure the temperature of the surface of the infrared energy generating system 14. The microchip of the temperature controlling switch 46 is responsive to a predetermined temperature range and is configured to turn the power "on" when the temperature is below a predetermined level and to turn the power "off" when the temperature is above a predetermined temperature. The microchip may be obtained from IBM or Texas Instruments and can be preprogramed to operate at a preselected "on" and "off" temperature. The temperature controlling switch 46 may be obtained from Infra—Texnology as part number LOG 16242. A further advantage of the alternative embodiment depicted in FIG. 5 is a power source enabled indicator 48, which is comprised of an LED indicator connected to the power source 18 when the contacts 21 and 22 are coupled together with fastener 20. The power source enabled indicator 48 allows the person using the wrist cover 12 to determine whether the power source has been enabled such that power is transmitted to the infrared energy generating system 14.

Figure 6:
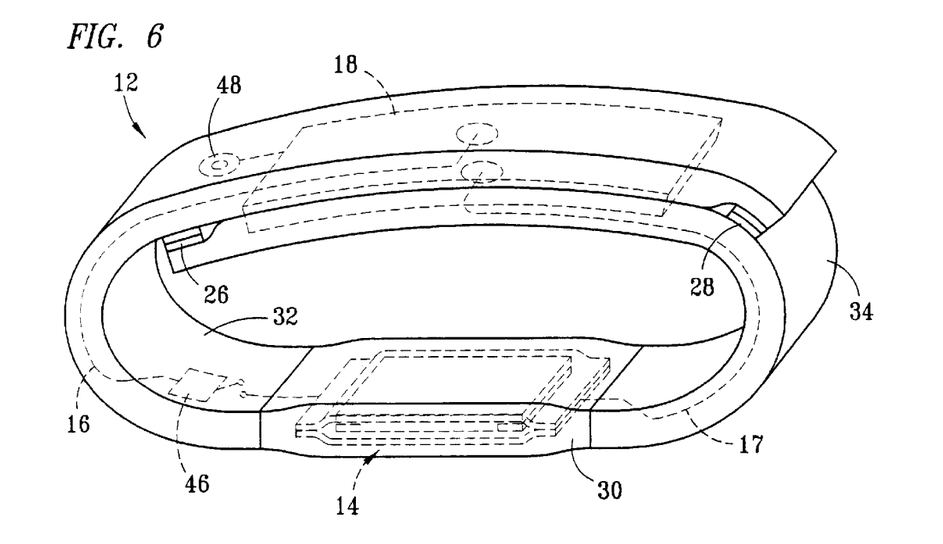
FIG. 6 is a side view schematic illustration of an alternative embodiment of an infrared emitting wrist cover showing the inclusion of a temperature controlling switch and a power source enabled indicator.

FIG. 6 is a side view schematic illustration of the alternative embodiment discussed in FIG. 5. FIG. 6 shows the placement of the temperature controlling switch 46 and the power source enabled indicator 48 within the second wrist cover band 34. The alternative embodiment shown in FIGS. 5 and 6 is but one embodiment including the temperature controlling switch 46 and the power source enabled indicator 48. The switch 46 is advantageously placed at the infrared energy generating system 14, either between the system 14 and the fastener 20 or securely encased in contact with the matrix 35 within the matrix enclosure 38. The enabled indicator 48 may be placed within the wrist cover 12 at a location for convenient observation by the user depending on the size, shape, and configuration of the wrist cover 12 design.

Figure 7:
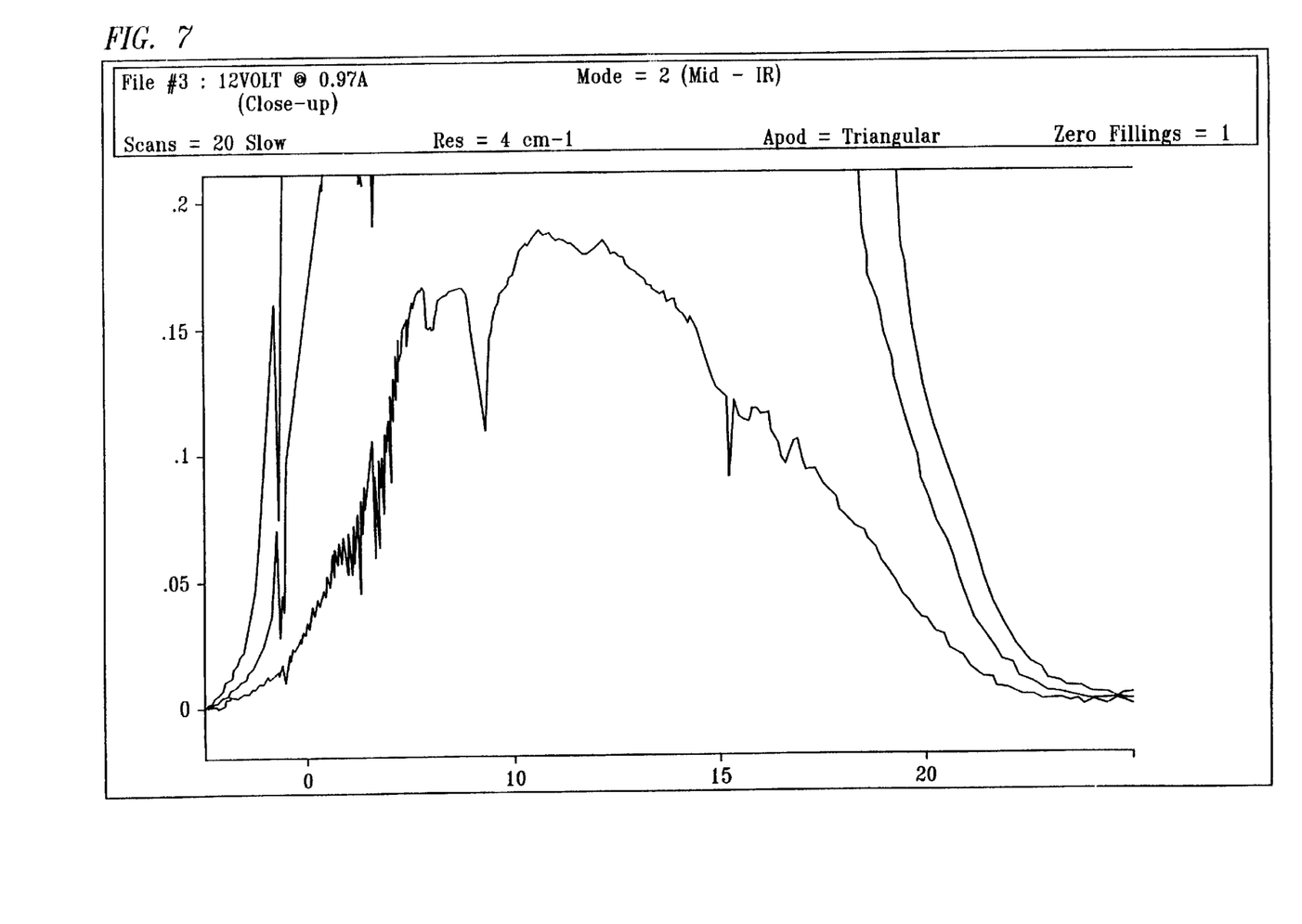
FIG. 7 is a graphical representation of the intensity of the infrared energy versus the wavelength of the energy for a power supply of 12 volts and for a specified composition of materials in the infrared energy generating matrix.

FIG. 7 is a graphical representation of the intensity of the infrared energy generated by the infrared energy generating system 14 versus the wavelength of the infrared energy for a power supply of 12 volts. Depending on the composition of the graphite-Teflon mixture of the infrared energy generating matrix 35, the matrix 35 will generate more or less energy intensity for a given power source 18. Battery power sources between 1 and 12 volts are contemplated to provide adequate energy without risk of electrical shock to the user. The unique capability of providing the desired energy intensity by preselecting the mixture of graphite and Teflon for the matrix 35 allows for a wide range of energy generating capabilities from the inventive wrist cover 12.

Figure 8:
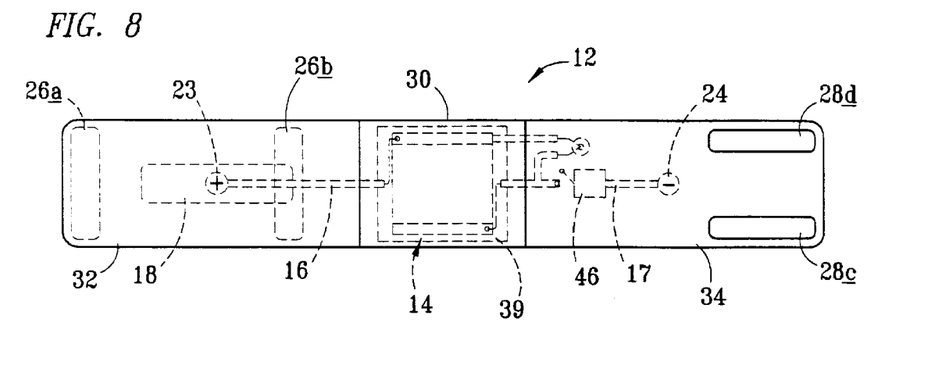
FIG. 8 is a top view schematic illustration of another alternative embodiment of an infrared emitting wrist cover showing the inclusion of a temperature controlling switch and a power source enabled indicator as well as alternative arrangements for the fastening devices and an alternative construction of the power strips for the infrared energy generating device.
Figure 9:
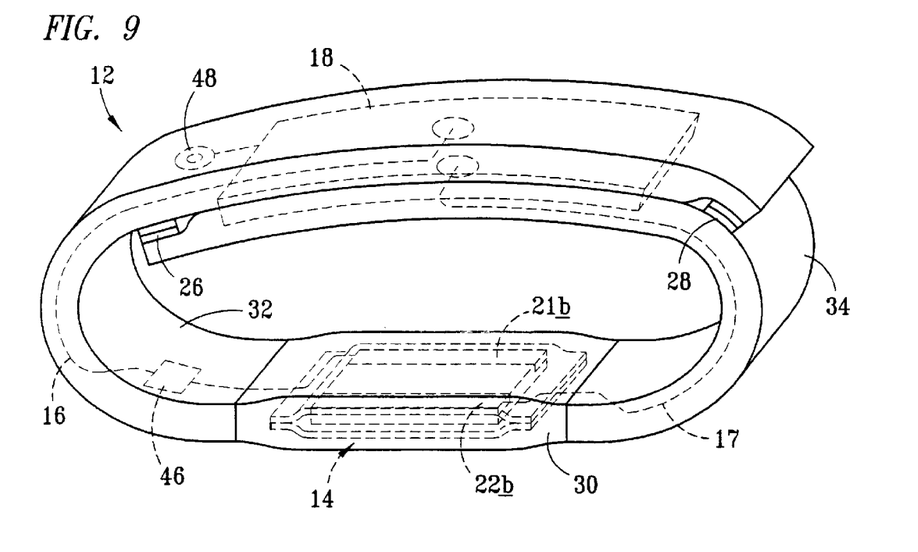
FIG. 9 is a side view schematic illustration of the alternative embodiment of an infrared emitting wrist cover of FIG. 8.

FIG. 8 is a side view schematic and FIG. 9 is a schematic perspective view of yet another alternative embodiment in which alternative variations of the orientations of the power strips 21b and 22b are parallel to each other and aligned with the length of the wrist cover bands 32 and 34. Also depicted is a length of band 32 covered with an elongated section of first fastener material 26c and lengthwise portions of second fastener material 28c and 28d. In this arrangement the fit of the wrist cover can be conveniently adjusted. Electrical contact 23b is elongated and opposite contact 24 can be held in electrical contact to provide power from power source 18. A switch 46 can also be provided to selectively activate the generation of infrared energy. An indicator light 48 is provided to be activated whenever electrical energy is connected to the infrared energy generator 14. The combinations depicted here demonstrate that any number of combinations of the selected features from the various embodiments depicted are intended to be within the scope of the invention as set forth in the claims.

While this invention has been described with a reference to illustrative embodiments, these descriptions are not intended to be construed in a limiting sense. Various modifications and combinations of the illustrative embodiments, as well as other embodiments of the invention, will be apparent to persons skilled in the art upon reference to the description. It is, therefore, intended that the appended claims encompass any such modifications or embodiments as may be fairly construed as with in the scope of the claims including variations with equivalent elements arranged to provide substantially the same functions in substantially the same way as the claimed invention.

What is claimed is:

1. An infrared energy emitting therapeutic device comprising:

a wrist cover;

a power source within said wrist cover;

an infrared energy generating system contained within said wrist cover and operatively connected to said power source for providing localized heat inside a wrist area for the purpose of relieving pain and reducing trauma associated with carpal tunnel syndrome a fastener having a first and a second fastening device for removably holding said wrist cover securely on a wrist; and cooperating contacts for connecting said infrared energy generating system to said power source upon connecting said first and second fastening devices.

2. An infrared energy emitting therapeutic device comprising:

a wrist cover;

a power source within said wrist cover;

an infrared energy generating system comprising an infrared energy generating matrix contained within said wrist cover and operatively connected to said power source for providing localized heat inside a wrist area for the purpose of relieving pain and reducing trauma associated with carpal tunnel syndrome; and a matrix enclosure at least partially surrounding said infrared energy generating matrix for the purpose of providing localized heat inside the wrist area without significantly increasing the temperature of said wrist cover.

3. The infrared energy emitting wrist cover as recited in claim 2 further comprising a reflective element external to said infrared energy generating matrix for the purpose of reflecting infrared energy into the wrist area.

4. An infrared energy emitting wrist cover comprising:

a wrist cover;

a wrist cover fastener; a power source;

power transmission wires;

an infrared energy generating system, wherein said power transmission wires connect said power source to said infrared energy generating system, for providing localized heat inside the wrist area for the purpose of relieving pain and reducing trauma associated with carpal tunnel syndrome, wherein said infrared energy generating system comprises an infrared energy generating matrix connected to said power source; and a matrix enclosure at least partially surrounding said infrared energy generating matrix within said wrist cover for the purpose of providing localized heat inside the wrist area without significantly increasing the temperature of the wrist cover.

5. The infrared energy emitting wrist cover as recited in claim 4 further comprising a reflective element external to said matrix enclosure for the purpose of reflecting infrared energy into the wrist area.

6. The infrared energy emitting wrist cover as recited in claim 4 wherein said power source is connected to a first and a second power strip for the purpose of supplying electrical current through said infrared energy generating matrix.

7. The infrared energy emitting wrist cover as recited in claim 6 wherein said power source is comprised of a replaceable battery in the shape of a portion of an arc for the purpose of fitting the curvature of said wrist cover when fastened around a wrist.

8. An infrared energy emitting wrist cover comprising: a wrist cover having a first wrist cover band and a second wrist cover band located between an infrared energy generating system housing, and having a first fastening device attached to said first wrist cover band, and a second fastening device attached to said second wrist cover band for fastening said wrist cover around a wrist;

a power source comprising a replaceable battery and having a first and a second electrical contact, a first and a second power strip, and power transmission wires for transmitting power when said wrist cover is fastened around a wrist; and an infrared energy generating system having an infrared energy generating matrix contained in a matrix enclosure, with a reflective element external to said matrix enclosure, and positioned within an infrared energy generating system housing such that, when said power source supplies power to said infrared energy generating system, said infrared energy generating system emits infrared energy into the wrist area for providing localized heat inside the wrist area for the purpose of relieving pain and reducing trauma associated with carpal tunnel syndrome.

9. The infrared energy emitting wrist cover as recited in claim 8 further comprising a temperature controlling switch for the purpose of enabling said power source when a preset minimum temperature is reached and disabling the power source when a preset maximum allowable temperature is reached.

10. The infrared energy emitting wrist cover as recited in claim 9 further comprising a power source enabled indicator for the purpose of indicating when said power source is providing power to said infrared energy generating system.

11. The infrared energy emitting wrist cover as recited in claim 8 further comprising a power source enabled indicator for the purpose of indicating when said power source is providing power to said infrared energy generating system.

* * * * *